(12) United States Patent  
Campen et al.

(10) Patent No.: US 8,433,416 B2
(45) Date of Patent: *Apr. 30, 2013

(54) METHOD AND APPARATUS FOR PROVIDING COMPLEX TISSUE STIMULATION PATTERNS

(75) Inventors: George Van Campen, Ft. Lauderdale, FL (US); John Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,419

(22) Filed: Jun. 25, 2012

(65) Prior Publication Data

US 2012/0271378 A1    Oct. 25, 2012

Related U.S. Application Data

(63) Continuation of application No. 13/180,243, filed on Jul. 11, 2011, now Pat. No. 8,209,020, which is a continuation of application No. 12/508,453, filed on Jul. 23, 2009, now Pat. No. 7,979,132, which is a continuation of application No. 11/383,107, filed on May 12, 2006, now Pat. No. 7,584,000, which is a continuation of application No. 10/627,234, filed on Jul. 25, 2003, now Pat. No. 7,047, 079.

(60) Provisional application No. 60/398,704, filed on Jul. 26, 2002, provisional application No. 60/398,749, filed on Jul. 26, 2002, provisional application No. 60/398,740, filed on Jul. 26, 2002, provisional application No. 60/400,366, filed on Aug. 1, 2002.

(51) Int. Cl.
*A61N 1/18* (2006.01)

(52) U.S. Cl.
USPC ............................................. 607/46; 607/16

(58) Field of Classification Search ............. 607/15, 607/16, 29, 46, 118
See application file for complete search history.

(56) References Cited

U.S. PATENT DOCUMENTS

| | | | |
|---|---|---|---|
| 3,738,371 A | 6/1973 | Raddi et al. |
| 4,326,534 A | 4/1982 | Axelgaard et al. |
| 4,390,022 A | 6/1983 | Calfee et al. |
| 4,407,972 A | 10/1983 | Brezny |
| 4,503,857 A | 3/1985 | Boute et al. |
| 4,535,777 A | 8/1985 | Castel |
| 5,058,582 A | 10/1991 | Thaler |
| 5,127,402 A | 7/1992 | Mann et al. |
| 5,350,412 A | 9/1994 | Hoegnelid et al. |
| 5,350,414 A | 9/1994 | Kolen |
| 5,354,320 A | 10/1994 | Schaldach et al. |
| 5,476,483 A | 12/1995 | Bornzin et al. |
| 5,540,730 A | 7/1996 | Terry, Jr. et al. |
| 5,745,352 A | 4/1998 | Sandri et al. |

(Continued)

FOREIGN PATENT DOCUMENTS

WO        8707511      12/1987

*Primary Examiner* — Joseph Dietrich

(57) ABSTRACT

The invention relates to a stimulation device for creating complex or multi-purpose tissue stimulation. Many typical stimulation devices suffer from deficiencies in providing complex stimulation patterns. Using a circuitry operable or programmable to repeat and skip stimulation settings, a complex stimulation set may be created. The repeating and skipping functionality may be implemented in hardware or software. In this manner, complex stimulations may be derived from simple circuitries. Furthermore, these stimulations may be used to treat pain, stimulate bone growth, and control motor disorders, among others.

6 Claims, 5 Drawing Sheets

U.S. PATENT DOCUMENTS

| | | | |
|---|---|---|---|
| 5,973,945 A | 10/1999 | Balakrishnan et al. | |
| 6,099,479 A | 8/2000 | Christopherson et al. | |
| 6,141,583 A | 10/2000 | Pape et al. | |
| 6,185,454 B1 | 2/2001 | Thompson | |
| 6,223,080 B1 | 4/2001 | Thompson | |
| 7,047,079 B2 | 5/2006 | Erickson | |
| 7,979,132 B2 | 7/2011 | Erickson | |
| 8,209,020 B2 | 6/2012 | Erickson | |

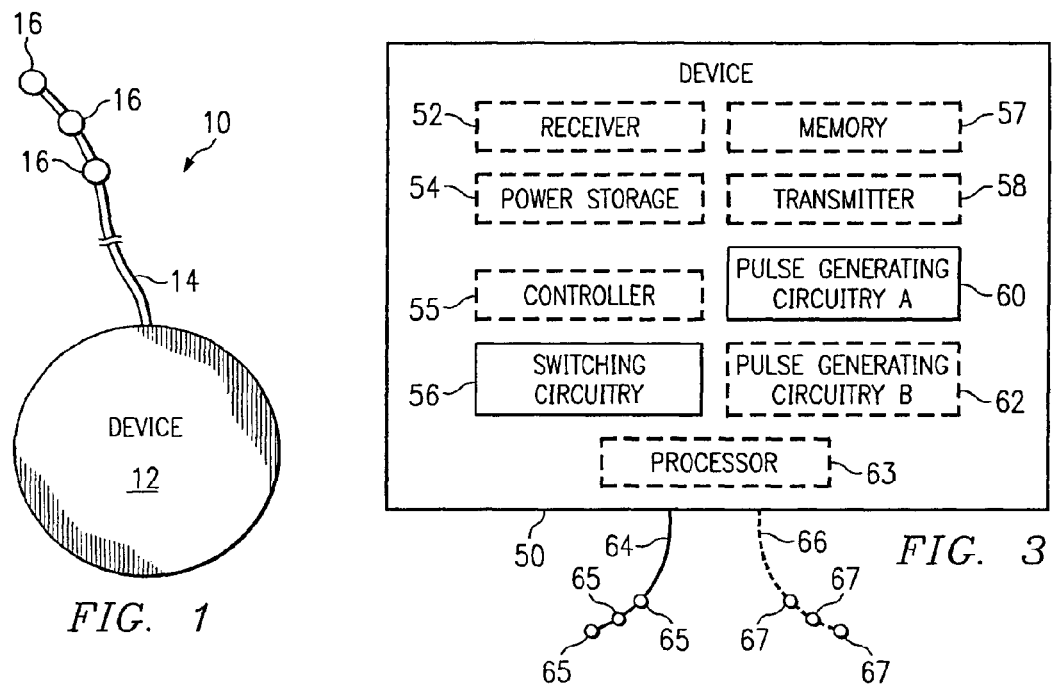
FIG. 1
FIG. 3
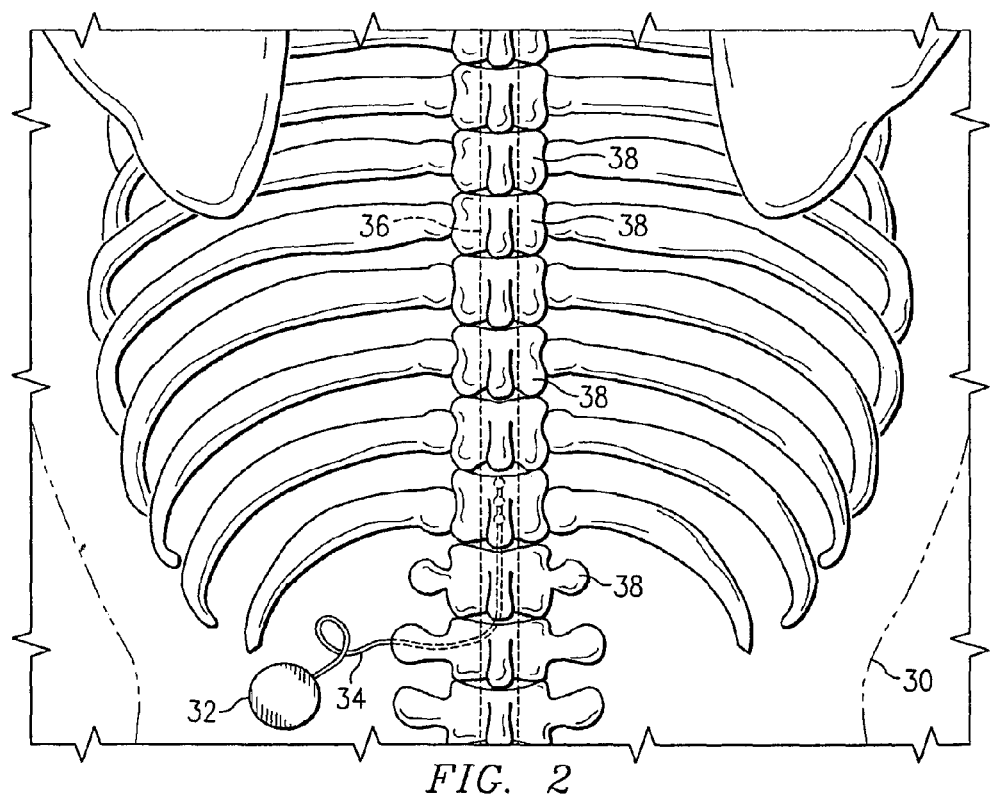
FIG. 2

FIG. 8A
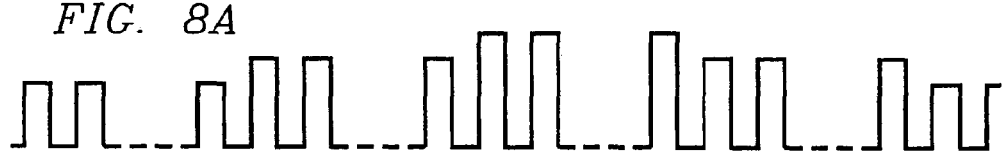
FIG. 8B
FIG. 8C
FIG. 8D
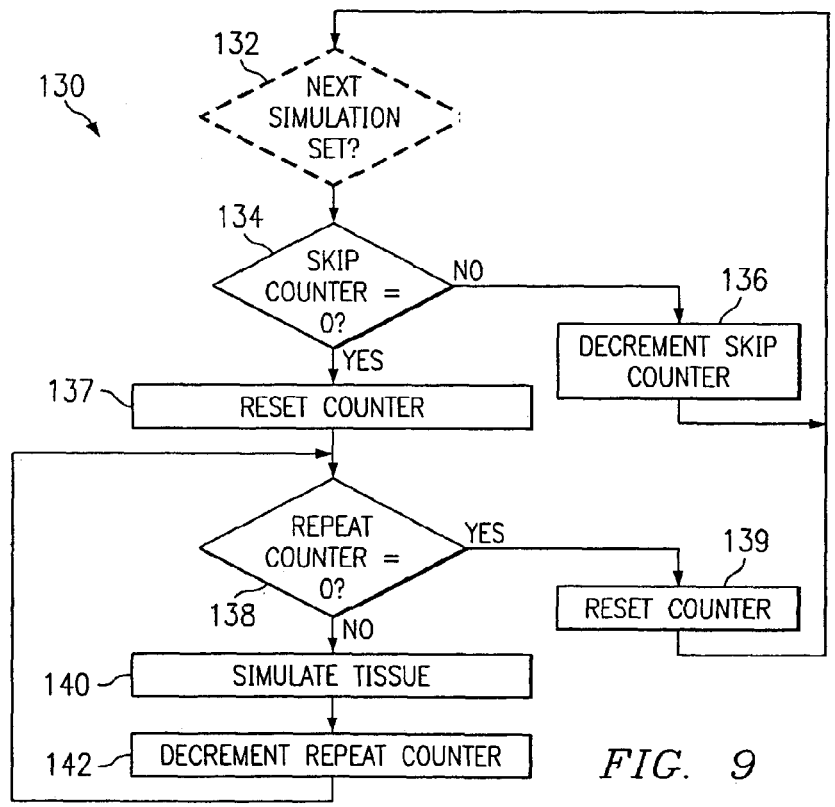
FIG. 9

METHOD AND APPARATUS FOR PROVIDING COMPLEX TISSUE STIMULATION PATTERNS

CROSS-REFERENCE TO RELATED APPLICATIONS

This application is a continuation of U.S. application Ser. No. 13/180,243, filed Jul. 11, 2011, now U.S. Pat. No. 8,209,020, which is a continuation of U.S. application Ser. No. 12/508,453, filed Jul. 23, 2009, now U.S. Pat. No. 7,979,132, which is a continuation of U.S. application Ser. No. 11/383,107, filed May 12, 2006, now U.S. Pat. No. 7,584,000, which is a continuation of U.S. application Ser. No. 10/627,234, filed Jul. 25, 2003, now U.S. Pat. No. 7,047,079, and this application also claims the benefit of (i) U.S. Provisional Patent Application No. 60/398,704, filed Jul. 26, 2002; (ii) U.S. Provisional Patent Application No. 60/398,749, filed Jul. 26, 2002; (iii) U.S. Provisional Patent Application No. 60/398,740, filed Jul. 26, 2002; and (iv) U.S. Provisional Patent Application No. 60/400,366, filed Aug. 1, 2002, the disclosures of which are incorporated herein by reference.

TECHNICAL FIELD OF THE INVENTION

This invention relates to a method and apparatus for tissue stimulation. More specifically, this invention relates to a method for creating complex stimulation patterns with a stimulation device coupled to one or more leads with one or more electrodes.

BACKGROUND OF THE INVENTION

Electronic stimulation systems may be used to control pain or motor disorders. Such systems have also been used to stimulate bone growth.

For example, application of an electrical field to spinal nervous tissue can effectively mask certain types of pain transmitted from regions of the body associated with the stimulated tissue. More specifically, applying particularized electrical pulses to the spinal cord associated with regions of the body afflicted with chronic pain can induce paresthesia, or a subjective sensation of numbness or tingling, in the afflicted bodily regions. This paresthesia can effectively inhibit the transmission of non-acute pain sensations to the brain.

Electrical energy, similar to that used to inhibit pain perception, may also be used to manage the symptoms of various motor disorders, for example, tremor, dystonia, spacticity, and the like. Motor spinal nervous tissue, or nervous tissue from ventral nerve roots, transmits muscle/motor control signals. Sensory spinal nervous tissue, or nervous tissue from dorsal nerve roots, transmit pain signals.

Electrical energy may be commonly delivered through electrodes positioned external to the dural layer surrounding a spinal cord. The electrodes are carried by two primary vehicles: the percutaneous lead and the laminotomy lead.

Percutaneous leads commonly have two or more electrodes and are positioned within an epidural space through the use of an insertion, or Touhy-like, needle. An example of an eight-electrode percutaneous lead is an OCTRODE® lead manufactured by Advanced Neuromodulation Systems, Inc. of Allen, Tex.

Operationally, an insertion needle is passed through the skin, between the desired vertebrae, and into an epidural space which is defined by a dural layer in combination with the surrounding vertebrae. The stimulation lead is then fed through the bore of the insertion needle and into the epidural space. Conventionally, the needle is inserted at an inferior vertebral position, for example, between vertebrae L1 and L2 (Li/L2), and the stimulation lead is advanced in a superior direction until the electrodes of the stimulation lead are positioned at a desired location within the epidural space, for example, at T10. In a lateral position, percutaneous leads are typically positioned about a physiological midline.

As an example of application, the above methodology is commonly used for the management of sympathetically maintained pain (SMP). It is generally believed that due to the sympathetic nature of SMP, stimulation leads positioned about a physiological midline provide sufficient electrical energy to interrupt the transmission of SMP signals. However, the above-described conventional technique may be used for the management of sympathetically independent pain (SIP), stimulating bone growth, and treating muscle disorders, among others.

As an alternative to spinal cord stimulation, electrical energy may be delivered to selected peripheral nerves using a peripheral nerve stimulation system. Peripheral nerve stimulation involves administration of electrical energy to a localized group of peripheral nerves through placement of one or more leads at the peripheral nerve site. Unfortunately, if a patient's pain is widespread, a patient may require a plurality of stimulation leads to be implanted. The surgical procedure necessary for stimulation lead implantation is significant and can be quite painful. Additionally, because peripheral stimulation leads are implanted in "active" areas of the body (e.g., arms and legs), the leads typically lack long-term placement stability. Lead movement, or lead migration, can affect the quality of pain relief. Further, significant lead movement that undermines the intended stimulation effect may require additional corrective surgeries to reposition the stimulation leads.

In each of these cases, the stimulation device may be coupled to one or more leads with one or more electrodes. Depending on the application and the purpose of the stimulation, varying stimulation patterns and electrical fields may be desired. An applied electrical field is defined by the polarity of each electrode of the stimulation lead. Conventionally, each electrode is set as an anode (+), cathode (−), or neutral (off). For a four electrode percutaneous lead there exists approximately 50 electrode combinations. For an eight electrode percutaneous lead, the number of possible electrode combinations grows to approximately 6050. Further, various combinations of pulses and pulse frequencies may be used with varying sets of electrodes.

Many typical stimulation devices are limited in their ability to deliver stimulations in complex patterns. Further, these typical stimulation devices may not be used in multi-purposes stimulation.

As such, many typical stimulation devices suffer from deficiencies in providing complex multi-purpose stimulation patterns. Many other problems and disadvantages of the prior art will become apparent to one skilled in the art after comparing such prior art with the present invention as described herein.

SUMMARY OF THE INVENTION

Aspects of the present invention may be found in a stimulation device for providing complex and/or multi-purpose stimulations to various tissues. The stimulation device may include a pulse generator, a switching circuitry, one or more means for pulse repetition, one or more means for pulse skipping, and one or more leads with one or more electrodes. The means for pulse repetition may include a counter and parameter. In addition, the means for pulse skipping may include a counter and parameter. Each repetition means and/ or skipping means may be associated with a stimulation setting. Further, these means may be implemented in hardware, software, or a combination of hardware and software.

Further aspects of the invention may be found in a method for stimulating tissue with complex and/or multi-purpose stimulation pulse patterns. A switching circuitry associated with the stimulation device may be configured to couple a particular electrode set. The set may be stimulated with a pulse from a pulse generator according to a stimulation setting. The pulse may be repeated in accordance with a repetition parameter. The switching circuitry or pulse characteristics may then be reconfigured in accordance with a subsequent stimulation setting. A pulse may then be generated in accordance with the subsequent stimulation setting. The subsequent setting may then be repeated and the settings reconfigured through an array of settings. Once the array of settings has been stimulated, the pattern may begin again. Or, in accordance with the skipping means, various settings may be skipped for subsequent stimulations of the array.

As such, an apparatus and method for complex and/or multi-purpose stimulation of tissue is described. Other aspects, advantages and novel features of the present invention will become apparent from the detailed description of the invention when considered in conjunction with the accompanying drawings.

BRIEF DESCRIPTION OF DRAWINGS

For a more complete understanding of the present invention and advantages thereof, reference is now made to the following description taken in conjunction with the accompanying drawings in which like reference numbers indicate like features and wherein:

FIG. 1 is a schematic diagram depicting a stimulation device;

FIG. 2 is a pictorial depicting an exemplary embodiment of a implanted stimulation device;

FIG. 3 is a schematic block diagram depicting an exemplary embodiment of a stimulation device;

FIG. 8A is a graph depicting an exemplary embodiment of a stimulation setting for use in the stimulation device of FIG. 3;

FIG. 8B is a graph depicting an exemplary embodiment of a stimulation setting for use in the stimulation device of FIG. 3;

FIG. 8C is a graph depicting an exemplary embodiment of a stimulation setting for use in the stimulation device of FIG. 3;

FIG. 8D is a graph depicting an exemplary embodiment of a stimulation setting for use in the stimulation device of FIG. 3; and FIG. 9 is a block flow diagram depicting an exemplary method for use by the system as seen in FIG. 1.

Corresponding reference numerals indicate corresponding parts throughout the several views of the drawings.

DETAILED DESCRIPTION OF DRAWINGS

Figure 4:
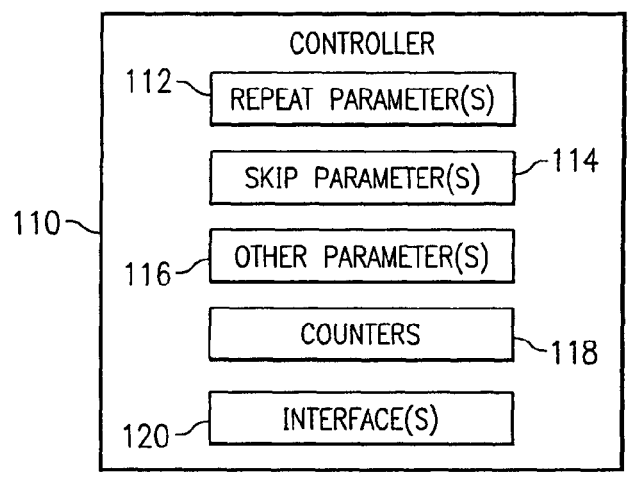
FIG. 4 is a schematic block diagram depicting an exemplary embodiment of a controller for use in the stimulation device of FIG. 3.

Several conditions may benefit from electrical pulse stimulation or modulation of tissue. These conditions include pain, bone growth, cardiac arrest and arrhythmias, peripheral vascular disease (PVD), angina pectoris, and various motor disorders. The electrical pulse stimulation can be delivered by a lead with several electrodes placed near the tissue to be stimulated. In this configuration, the lead is connected to a stimulation device, which is either implanted corporally or external to the body.

FIG. 1 is an exemplary implanted stimulation system 10. Device 12 may be implanted in a patient. Attached to device 12 is lead 14, which terminates in a set or array of electrodes 16. Device 12 may be used to treat various conditions such as arrhythmias, muscle tremors, tissue damage, and chronic pain, among others.

Device 12 may take various forms. These forms may include implanted pulse generators, neurostimulators, muscle stimulators, and defibrillators, among others.

Lead 14 and electrodes 16 may take various forms. These forms may include cylindrical leads and electrodes, paddles, and lamitrodes, among others. Lead 14 may have one or more electrodes 16 and these electrodes 16 may be shaped in accordance with various functions. Furthermore, more than one lead 14 may be attached to device 12.

Stimulation device 12 may be configured to stimulate one or more sets of electrodes with one or more pulses having various pulse characteristics. Together, the sets of electrodes and pulse characteristics make stimulation settings. For each stimulation setting, each electrode is set as an anode (+), cathode (−), or neutral (off). For a four electrode percutaneous lead there exists approximately 50 electrode combinations. For an eight electrode percutaneous lead, the number of possible electrode combinations grows to approximately 6050. These electrode settings are combined with pulse characteristics and pulse patterns to stimulate the tissue.

For example the device may act to stimulate the heart muscle, bone, spinal nervous tissue, other muscle tissue, and other nervous tissue, among others. FIG. 2 depicts an exemplary embodiment of a neurostimulator implanted in the torso 30 of an individual. In this exemplary embodiment, device 32 is installed such that lead 34 extends into the spinal foramen 36 as defined by the vertebrae 38. Lead 34 terminates with one or more electrodes. These electrodes are used to stimulate or modulate nervous tissue. The stimulation or modulation may function to prevent muscle tremor and/or mask pain. The function and location of effect may be affected by the location and stimulation characteristics of the electric field pulses delivered by device 32.

The stimulation activity and tissue type may be best suited to differing pulse patterns. For example, stimulation of bone growth may use periodic bursts of high frequency pulses. On the other hand, pain masking may require consistent pulsing at a lower frequency. Alternately, pain masking may be produced by patterns of varying pulse frequency and amplitude.

FIG. 3 is an exemplary embodiment of a stimulation device for creating complex and/or multi-purpose stimulation sets. The device 50 may have a receiver 52, transmitter 58, power storage 54, controller 55, switching circuitry 56, memory 57, pulse generators 60 and 62, and processor 63. Device 50 is typically coupled to one or more leads 64 and 66. Leads 64 and 66 terminate in one or more electrodes 65 and 67. However, some, all, or none of the components may be included in device 50. Further, these components may be together, separate, or in various combinations, among others.

Receiver 52 may take various forms. These forms may include a circuitry, antenna, or coil, among others. The receiver 52 may or may not function to receive instructions and data. Further, the receiver 52 may or may not function to receive power that may be used by the device and/or stored in the power storage 54. Similarly, the transmitter 58 may take various forms including a circuitry, antenna, or coil, among others. The transmitter 58 may function to transmit data and/or instructions. However, the receiver 52 and transmitter 58 may or may not be included or may be together, separate, combine various components, among others.

The power storage 54 may take various forms. These forms may include various batteries.

Controller 55 may take various forms. These forms may include those discussed in FIG. 4 or other means for modulating and controlling pulses and signals. Further, aspects of controller 55 may be implemented as software, hardware, or a combination of software and hardware.

Switching circuitry 56 may take various forms. These forms may include various contacts, relays, and switch matrices, among others. Further, switching circuitry 56 may or may not include one or more blocking capacitors associated with connections to the leads. These blocking capacitors may block direct connection to the leads and/or function to build charge that may be discharged between signal pulses. Furthermore, switching circuitry 56 in combination with microprocessor 63 and/or controller 55 may function to drop, skip, or repeat stimulation patterns.

Memory 57 may take various forms. These forms may include various forms of random access memory, read-only memory, and flash memory, among others. The memory may be accessible by controller 55, the switching circuitry, and/or processor 63. Further, the memory may store various stimulation settings, repetition parameters, skipping parameters, programs, instruction sets, and other parameters, among others.

Processor 63 may take various forms. These forms may include logic circuitry or microprocessors, among others. Processor 63 may function to monitor, deliver, and control delivery of the modulation or stimulation signal. Further, processor 63 may manipulate switching circuitry 56. This manipulation may or may not be in conjunction with controller 55.

The one or more pulse generators 60 and 62 may take various forms. These forms may include a clock driven circuitry, or an oscillating circuitry, among others. The pulse generator(s) 60 and 62 may deliver a electric or electromagnetic signal through switching circuitry 56 to leads 64 and 66 and electrodes 65 and 67. The signal may be modulated by circuitry associated with the switching circuitry 56, controller 55, and/or processor 63 to manipulate characteristics of the signal including amplitude, frequency, polarity, and pulse width, among others.

In one exemplary embodiment, microprocessor 63 may interact with switching circuitry 56 to establish electrode configurations. The pulse generator may then generate a pulse and, in combination with microprocessor 63 and switching circuitry 56, stimulate the tissue with a pulse having desired characteristics. The controller 55 may interact with microprocessor 63 and switching circuitry 56 to direct the repetition of the pulse. Alternately, switching circuitry 56 may be reconfigured to subsequent stimulation settings in an array of stimulation settings. The controller 55 may then direct the skipping or with settings in the array of settings for one or more passes through the stimulation setting array. Controller 55 may be implemented as software for use by microprocessor 63 or in hardware for interaction with microprocessor 63 and switching circuitry 56, among others.

FIG. 4 is a schematic block diagram depicting an exemplary embodiment of a controller. The controller 110 may have one or more repeat parameters 112, one or more skip parameters 114, other parameters 116, counters 118, and interfaces 120.

The one or more repeat parameters 112 may be associated with one or more of the stimulation settings. For example, a stimulation device may have eight stimulation settings. Each of the eight stimulation settings may have a repeat parameter 112 associated with it. Alternately, a repeat parameter 112 may be associated with a given stimulation setting such as a first stimulation setting. The repeat parameter 112 may cause a given stimulation setting to repeat a number of times in accordance with the repeat parameter 112.

Similarly, skip parameters 114 may be associated with one or more of the stimulation settings. Each of the eight stimulation settings may have a skip parameter 114 associated with it. Alternately, a skip parameter 114 may be associated with a given stimulation setting such as a first stimulation setting. Skip parameter 114 may cause a given stimulation setting to be dropped or skipped for a given number of cycles through the array of stimulation settings in accordance with skip parameter 114. Various other parameters 116 may also be associated with controller 110.

In addition, various counters 118 may be associated with controller 110. These counters 118 may be used in determining which pulses or stimulation sets to skip or when to stop repeating a stimulation set.

Further, controller 110 may have various interfaces 120. These interfaces enable communication with the switching circuitry, microprocessor, and pulse generator, among others. These interfaces may take the form of circuitry in the case of a hardware based controller. Alternately, these interfaces may take the form of software interfaces in the case of a software based controller. In addition, various combinations may be envisaged.

Figure 5:
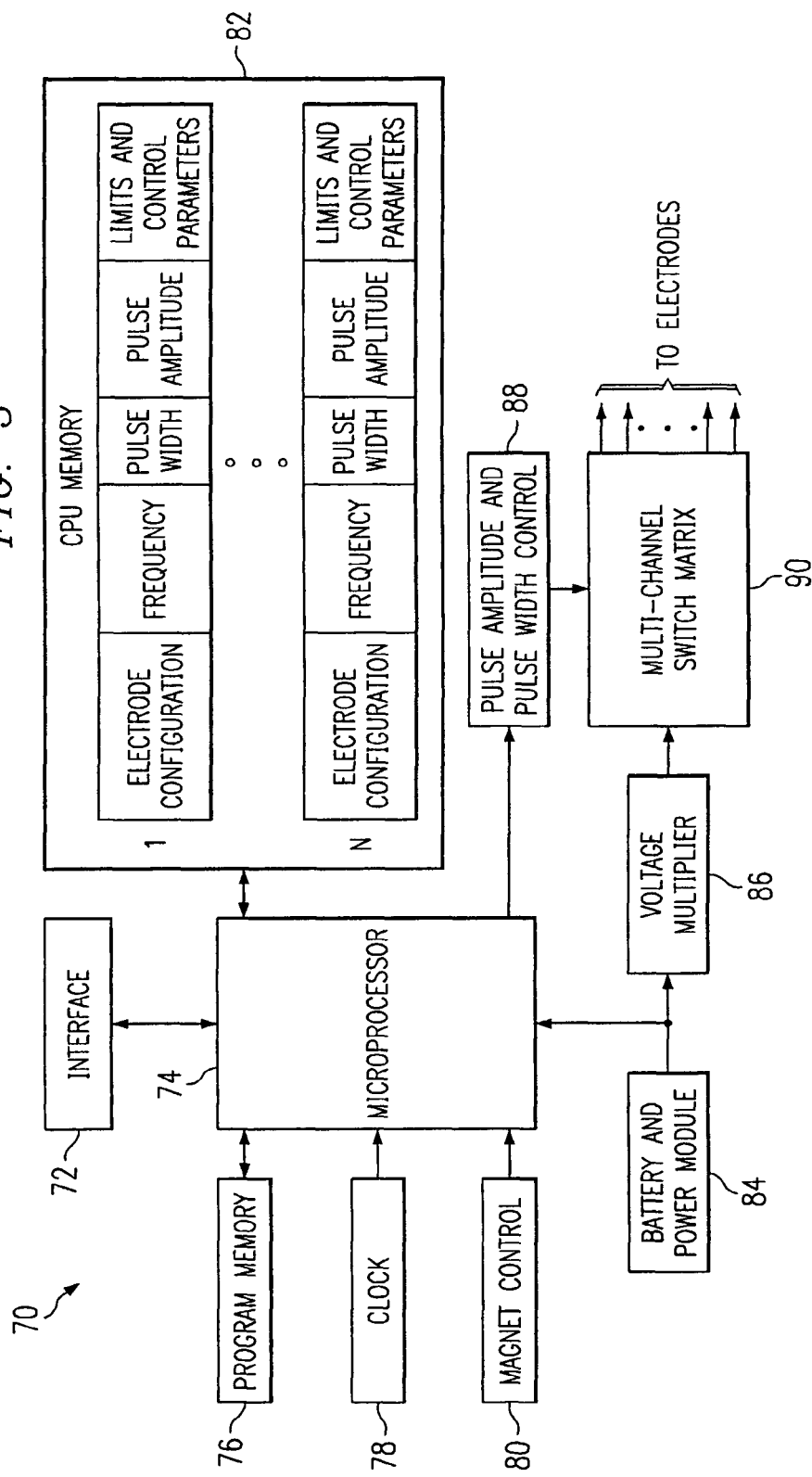
FIG. 5 is a schematic block diagram depicting an exemplary embodiment of the system as seen in FIG. 3.

FIG. 5 is a schematic block diagram depicting an exemplary embodiment of the system. This exemplary embodiment 70 may have a microprocessor 74, interface 72, program memory 76, clock 78, magnet control 80, power module 84, voltage multiplier 86, pulse amplitude and width control 88, CPU memory 82, and multi-channel switch matrix 90. However, these components may or may not be included and may be together, separate, or in various combinations.

Microprocessor 74 may take the form of various processors and logic circuitry and can function to control pulse stimulations in accordance with settings 1 through N stored in the CPU memory 82. Further, microprocessor 74 may function in accordance with programs stored in program memory 76.

Program memory 76 may take various forms. These forms may include RAM, ROM, flash memory, and other storage mediums among others. Further, program memory 76 may be programmed using interfaces 72.

These interfaces 72 may be accessed prior to implanting to program microprocessor 74, program memory 76, and or CPU memory 82. These forms may include ports or connections to handheld circuitry, computers, keyboards, displays, and program storage, among others. Alternately, interfaces 72 may include means for interaction and programming after implanting.

Clock 78 may be coupled to microprocessor 74. Clock 78 may provide a signal by which microprocessor 74 operates and/or uses in creating stimulation pulses.

Magnet control 80 may also interface with microprocessor 74 and functions to start or stop stimulation pulses. Alternately, a receiver or other means may be used to accomplish the same task. The receiver may or may not function to provide programming instruction, power charge, and on/off signals.

System 70 may also have a power supply or battery 84. This power supply 80 may function to power the various circuitries such as clock 78, microprocessor 74, program memory 76, and CPU memory 82, among others. Further, power supply 80 may be used in generating the stimulation pulses. As such, the power supply may be coupled to the microprocessor 74, a voltage multiplier, and/or a switch matrix 90.

CPU memory 82 can take various forms, which may include RAM, ROM, flash memory, and other storage mediums among others. CPU memory 82 may store stimulation settings 1 through N. These stimulation settings may include electrode configuration, pulse frequency, pulse width, pulse amplitude, and other limits and control parameters. The repetition and skipping parameters can be stored in CPU memory 82 and may be associated with each of the stimulation settings 1 through N. Microprocessor 74 may uses these stimulation settings and parameters in configuring switch matrix 90, manipulating pulse amplitude and pulse width control 88, and producing stimulation pulses.

Switch matrix 90 may permit more than one lead with more than one electrode to be connected to system 70. Switch matrix 90 may function with other components to selectively stimulate varying sets of electrodes with various pulse characteristics.

In this exemplary embodiment, the controller may be implemented in software for interpretation by microprocessor 74. Alternately, a hardware implementation may be coupled to microprocessor 74, pulse amplitude controller 88, and switch matrix 90. However, various embodiment of the controller, system 70, and implementation may be envisaged.

Figure 6A:
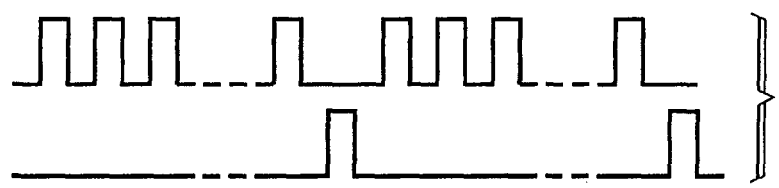
FIG. 6A is a graph depicting an exemplary embodiment of a stimulation setting for use in the stimulation device of FIG. 3.

The repetition means as seen in relation to the controller of FIG. 4 or microprocessor 74 of FIG. 5 enables a stimulation set to be repeated before switching to a different stimulation set or pulse characteristic. FIG. 6A is a graph depicting an exemplary embodiment of stimulation sets. In this embodiment, the first stimulation set may be repeated N number of times before the stimulation settings are changed to the next set. Subsequently, a pulse is directed in accordance with a second stimulation set after which the pattern is repeated.

Figure 6B:
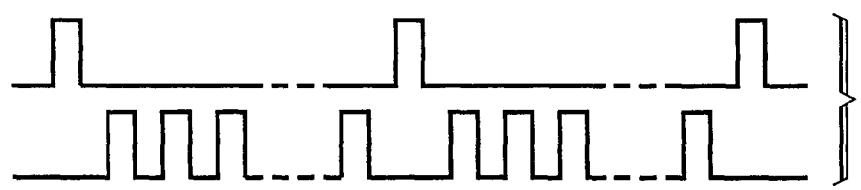
FIG. 6B is a graph depicting an exemplary embodiment of a stimulation setting for use in the stimulation device of FIG. 3.
Figure 6C:
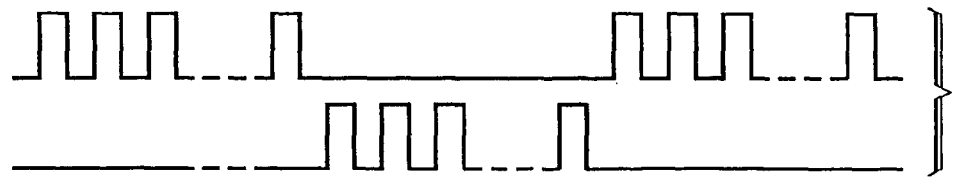
FIG. 6C is a graph depicting an exemplary embodiment of a stimulation setting for use in the stimulation device of FIG. 3.

In another exemplary embodiment, the first stimulation set is pulsed, followed by a repetition of the second set for N number of pulses as seen in FIG. 6B. In another embodiment, both sets may be pulsed for N number of pulses as seen in FIG. 6C. The sets may be pulsed differing number of times. In addition, more than two stimulation sets may be used.

Figure 7A:
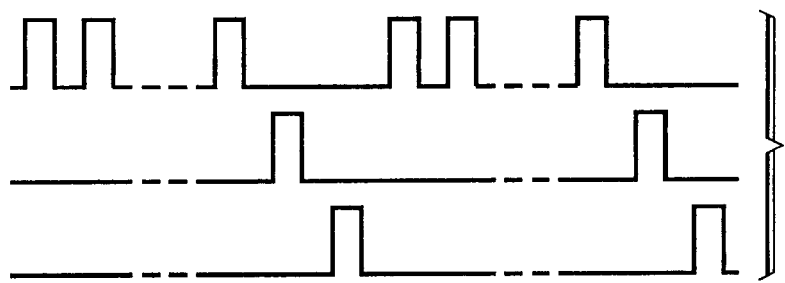
FIG. 7A is a graph depicting an exemplary embodiment of a stimulation setting for use in the stimulation device of FIG. 3.

FIG. 7A is a graph depicts another exemplary embodiment of an array of stimulation sets. In this case, the first stimulation set is repeated. This repetition may be achieved through a repetition means associated with the first set. Alternately, the apparent repetition may be achieved by dropping or skipping the second and third stimulation sets N number of cycles through the stimulation array.

Figure 7B:
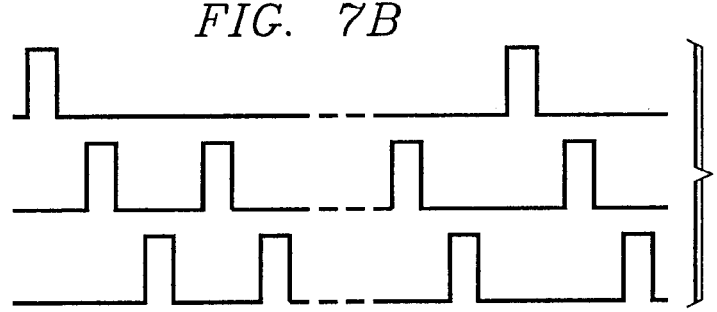
FIG. 7B is a graph depicting an exemplary embodiment of a stimulation setting for use in the stimulation device of FIG. 3.

FIG. 7B shows the effect of skipping the first stimulation set N number of cycles through the stimulation array. The first stimulation set is pulsed, followed by the second then third stimulation sets. However, on the next cycle, the first stimulation set is skipped. The first stimulation set may be skipped N number of cycles in accordance with the skipping means or parameters.

Figure 7C:
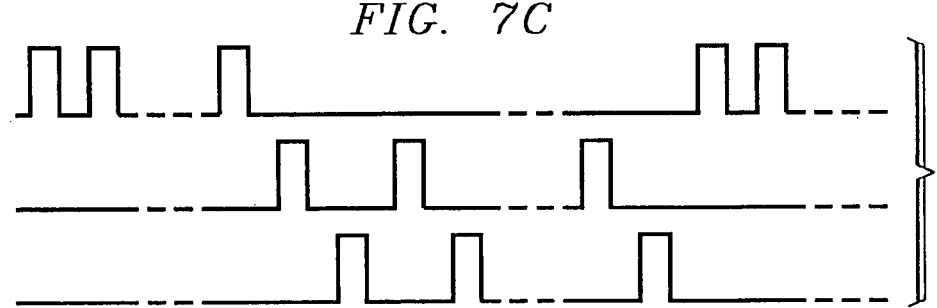
FIG. 7C is a graph depicting an exemplary embodiment of a stimulation setting for use in the stimulation device of FIG. 3.

In another exemplary embodiment seen in FIG. 7C, the skipping and repetition means and methods may be combined to form a more complex pattern. In this case, the first stimulation setting receives a repeated pulse. Subsequently, the array cycles through the second then third stimulation settings. However, the first pulse is skipped for the next N cycles. The pattern is then repeated with a repeated first pulse, followed by a cycling, followed by the skipping of the first stimulation set.

The skipping and repeating means and methods may also be used to augment the stimulation of a single electrode set with varying pulse characteristics. FIG. 8A depicts a pulse pattern placed on a single electrode set. The pulse pattern repeats a first pulse characteristic. In this example, the amplitude is shown to vary. Subsequently, the amplitude is changed for a second stimulation that may be repeated. Further stimulation sets may have various characteristics through the cycle of the array. In the example seen in FIG. 8A, the four sets may be seen as step changes in amplitude before the cycle is repeated.

In another exemplary embodiment, pulses may be skipped to effectively change the frequency of the pulse. FIG. 8B shows a single set of electrodes receiving a stimulation in which a first pulse characteristic is repeated, then skipped. In this case, the apparent frequency change may be implemented as two stimulation sets, one being repeated then skipped. Alternately, the pattern may be achieved through other combinations of repetition and skipping.

FIG. 8C shows a combination of changing frequency and amplitude on a single set of electrodes. This example may also be implemented as two stimulation sets utilizing the repetition and skipping features.

In another exemplary embodiment, FIG. 8D depicts the use of stimulation sets which differ in pulse width characteristics. However, various combinations of stimulation settings may be used in conjunction with the repetition means and the skipping means. These combinations may be customized to specific applications.

An exemplary method for use by the system is seen in FIG. 9. The method 130 may or may not include a step of reconfiguring the system for the next stimulation set as seen in block 132. In a system with multiple stimulation sets, the system may select the next stimulation set in an array. Alternately, the system may only apply the method to one stimulation set in the array.

The system then determines the presence or value of a skip counter and act accordingly as seen in block 134. In the case of a decrementing counter, the test may be to determine if the counter is non-zero. However, an incrementing counter may be used for which, the test would be to determine if the counter value is equal to a skip parameter is achieved. On the other hand, in cases where a stimulation set is not present for a specific stimulation set, the system may skip to another step.

If the skip counter is not zero in the case of a decrementing counter or has not reached the value of the skip parameter in the case of an incrementing counter, the system may decrement or increment the counter, respectively, as seen in block 136. Effectively, the pulse or stimulation is skipped or dropped. Then, the next stimulation set may be selected as seen in block 132.

If the skip counter has reached the appropriate value, the counter may be reset as seen in block 137. For a decrementing counter, the counter may be reset to the skip parameter value. For an incrementing counter, the counter may be reset to zero.

The system then tests for a repeat counter and its value as seen in block 138. In the case of a decrementing counter, the system tests to determine if the counter is zero. Alternately, in the case of an incrementing counter, the system tests to determine if the counter has reached the repeat parameter value.

If the counter has not reached to appropriate value, the system stimulates the tissue in accordance with the stimulation set as seen in block 140. The counter is then decremented if it is a decrementing counter or incremented if it is an incrementing counter as seen in block 142. The system then tests the value of the counter again as seen in block 138.

However, if the counter has reached the desired value, the system resets the counter as seen in block 139. If the counter is a decrementing counter, the counter may be reset to the repeat parameter value. However, if the counter is an incrementing counter, the counter may be reset to zero. Subsequently, the system may select the next stimulation set as seen in block 132.

However, these steps may or may not be included in the method. Further, the steps may be arranged in various sequences.

As such, a stimulation device for creating complex and/or multi-purpose tissue stimulation is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed:

1. A method of treating a neurological condition involving motor disorder in a patient, the method comprising:
    programming an implantable implantable neurostimulator, that is implanted in the patient, to operate according a plurality of stimulation settings, wherein each stimulation setting comprises a pulse amplitude parameter, an electrode combination parameter, and a pulse repetition parameter;
    operating the implantable neurostimulator to generate electrical pulses according to the plurality of stimulation settings for application to nervous system tissue of the patient in an manner that is effective in reducing tremor in the patient, wherein during operation the implantable neurostimulator (i) repetitively, for a respective stimulation setting, compares the pulse repetition parameter against a number of pulses generated for the respective stimulation setting; (ii) generates and outputs a stimulation pulse for the current stimulation setting according to the pulse amplitude parameter and the electrode combination parameter of the current stimulation setting when a comparison, of the pulse repetition parameter against a number of pulses generated, determines that a sufficient number of pulses have not been generated, (iii) proceeds to a succeeding stimulation setting without generating another stimulation pulse for the current stimulation program when the comparison, of the pulse repetition parameter against a number of pulses generated, determines that a sufficient number of pulses have been generated, and (iv) performs a cycle reset after a completing pulses for a last stimulation setting of the plurality of stimulation settings.

2. The implantable neurostimulator of claim 1 wherein the implantable pulse generator maintains a counter in memory for counting a number of stimulation pulses for a current stimulation setting.

3. The implantable neurostimulator of claim 1 wherein the implantable pulse generator maintains a counter in memory for counting a number of stimulation pulses for all of the plurality of stimulation settings to determine when to perform a pattern reset.

4. The implantable neurostimulator of claim 1 wherein at least one pulse repetition parameter of the plurality of stimulation settings is set in a random manner.

5. The implantable neurostimulator of claim 1 wherein each stimulation setting comprises a skipping parameter that defines a rate of occurrences of pulse skipping for a respective stimulation setting within a repeating pattern of pulses.

6. The implantable neurostimulator of claim 1 wherein pulse width is varied between respective pulses for a respective stimulation setting.

* * * * *